United States Patent
Neuberger (10) Patent No.: US 8,180,444 B2
(45) Date of Patent: May 15, 2012

(54) ENHANCED PHOTODYNAMIC THERAPY WITH IMMUNE SYSTEM ASSIST

(75) Inventor: Wolfgang Neuberger, F.T. Labuan (MY)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 0 days.

(21) Appl. No.: 12/144,294

(22) Filed: Jun. 23, 2008

(65) Prior Publication Data
US 2009/0062719 A1    Mar. 5, 2009

Related U.S. Application Data

(60) Provisional application No. 60/937,034, filed on Jun. 22, 2007.

(51) Int. Cl.
*A61N 1/30* (2006.01)
(52) U.S. Cl. .............. 604/20; 604/501; 607/89; 607/88; 606/3
(58) Field of Classification Search .................. 604/20, 604/500, 501, 21; 514/185; 424/278.1, 282.1; 607/88, 89
See application file for complete search history.

(56) References Cited

U.S. PATENT DOCUMENTS

| | | |
|---|---|---|
| 5,865,840 A | 2/1999 | Chen |
| 6,290,712 B1 | 9/2001 | Nordquist |
| 6,495,585 B2 | 12/2002 | Bellnier |
| 2002/0004053 A1 | 1/2002 | Biel |
| 2004/0147501 A1 | 7/2004 | Dolmans |
| 2005/0187207 A1 | 8/2005 | Curry |
| 2008/0195032 A1* | 8/2008 | Nifantiev et al. ............... 604/20 |

* cited by examiner

*Primary Examiner* — Jackie Ho
*Assistant Examiner* — Imani Hayman
(74) *Attorney, Agent, or Firm* — B J Associates; Bolesh J. Skutnik (57) ABSTRACT

A photodynamic therapy (PDT) method to treat primary sites of hyperproliferative tissue and induce long term, tumor specific immunity for regression and eradication of distant metastases is disclosed. The improved treatment regimen comprises the partial or fractional application of PDT with several applications, spaced in time, to permit a patient's immune system to react to dead tissue generated by each fractional application. Once activated, the immune system can help reduce or eliminate secondary stage tumors and metastasis stage tumors.

25 Claims, 2 Drawing Sheets

ENHANCED PHOTODYNAMIC THERAPY WITH IMMUNE SYSTEM ASSIST

CROSS-REFERENCE TO RELATED APPLICATION

This application claims priority under 35 U.S.C. §119(e) to U.S. Provisional Patent Application Ser. No. 60/937,034, filed Jun. 22, 2007, entitled "Enhanced PhotoDynamic Therapy with Immune System Assist," which is hereby incorporated by reference in its entirety as part of the present disclosure.

FIELD OF INVENTION

The present invention generally concerns the field of PhotoDynamic Therapy for cancer treatment. In particular, the present invention targets tumors, for example, primary tumors, secondary tumors and metastatic tumors by stimulating the immune system.

BACKGROUND

PhotoDynamic Therapy (PDT) is a relatively new method useful for treating various types of malignant and non-malignant hyperproliferative diseases, for example, cancers and hyperplasias. Certain photodynamic compounds, called photosensitizers (PS), have the ability to selectively accumulate in hyperproliferative tissue as compared to normal tissue. When administered, these PS accumulate in hyperproliferative tissue and absorb light. Light absorption causes the PS to destroy hyperproliferative tissue. Activated PS tissue destruction is known as PDT.

The PS are administered to the subject by a suitable method in order to accumulate in the hyperproliferative tissue. Photosensitizers are activated by electromagnetic radiation, for example, laser radiation delivered through fiber optics to cause cytotoxicity in hyperproliferative tissue, such as, the production of singlet oxygen. The oxygen radicals are toxic to the cells and induce cellular destruction via necrosis or apoptosis.

Unfortunately, current PDT approaches suffer from several well-known, and widely recognized shortcomings. For example, certain therapeutic approaches require the invasive placement of a light source in or adjacent to the abnormal tissue to be treated. The invasive nature of such procedures is undesirable for obvious reasons, for example, the need for local or general anesthetics, higher risk of infection, increased pain and discomfort, and longer recovery times. Additional procedures that are currently available require the co-administration (i.e., either simultaneous or sequential) of the PS agent with one or more immuno-adjuvants and/or immunopotentiators. The use of immunoadjuvants or immunopotentiators is problematic because they can have detrimental side-effects, including, for example, severe immunogenic responses, and adverse molecular interactions within a patient. Such adverse events can lead to longer and more costly patient treatment and recovery durations.

In U.S. Pat. No. 5,865,840 by Chen, a plurality of PDT treatments are disclosed that follow at least one initial treatment, characterized by an increase in neutrophil count achieved by administering a myeloid colony stimulating factor after the first treatment. The light source used here is either implanted in the abnormal tissue or disposed adjacent to the abnormal tissue, which are additional and invasive steps that could cause discomfort.

U.S. Patent Application 2005/0187207 by Curry et al. ("Curry") describes an immuno-adjuvant PDT to treat and prevent metastatic cancer. This therapy involves the administration of one or more PS and one or more immuno-adjuvants followed by irradiation with suitable wavelength. Selection of an in-proper immuno-adjuvant and interactions within a patient can lead to complex problems.

U.S. Patent Application 2002/0004053 by Biel et al. prescribes administration of an immunologic adjuvant to enhance a nonspecific immune system response, similar to Curry. Subsequently, the area is treated with appropriate radiation to destroy abnormal cells. Photosensitizer administration to the target tumor may spread to tissue surrounding the tumor causing excessive, non-therapeutic tissue damage. Repeated immuno-adjuvant administration could be associated with side effects and lengthy treatment duration.

U.S. Pat. No. 6,290,712 by Nordquist et al. discloses combination therapy of PDT and an immunopotentiator to stimulate the immune system. The immunopotentiator is a necessary component to stimulate an immune system inflammatory response.

U.S. Pat. No. 6,495,585 by Bellnier et al., discloses a method including the following steps: injecting a PS having a selective uptake in hyperproliferative tissue and activation at a particular light frequency; injecting xanthonone-4-acetic acid or a Group I metal, Group II metal or quaternary salt near the time of maximum uptake of the PS in hyperproliferative tissue; and exposing the hyperproliferative tissue to light that activates the PS. The method is stated to locally treat malignant tumors and stimulate tumor immunity resulting in the control of primary tumors and occult metastases by combining PDT with an additional agent for modifying a biological response.

As discussed above, certain strategies exist that attempt to stimulate the immune system in order to improve the efficacy of PDT. However, these attempts have all been characterized by the combined use of PDT and immunopotientators to stimulate an immune response. The present invention is advantageous over the current methods as it provides for improved PDT without the need for introducing an immunopotientator into the body, thereby eliminating concerns about the immunopotientator's adverse effects.

SUMMARY

The present invention is based upon the surprising and unexpected discovery of methods and compositions for inducing the destruction or degradation of primary localized hyperproliferative tissue through the administration of photodynamic therapy (PDT). The methods of the invention are clinically beneficial due, at least in part, to the accompanying stimulation of the patient's natural immune system without the requirement of administration of immuno-adjuvants or immunopotentiators. The concomitant stimulation of the natural immune system achieved through the methods of the invention provides further resistance against tumor development. As such, described herein are methods for the destruction of hyperproliferative and metastatic tumor tissue by photodynamic therapy (PDT) with immune system assistance.

In certain aspects, the methods of the invention include the administration of multiple PDT regimens within a suitable time interval. In one embodiment, the methods of the invention comprise the administration of a relatively low effective dosage of at least one PS agent followed by one or more suitable laser irradiations to partially degrade the hyperproliferative tissue and stimulate the inflammatory immune system response of phagocytosis.

In other aspects, the methods of the invention include the administration of a relatively high effective dosage of at least one PS agent followed by one or more laser irradiations to completely destroy the hyperproliferative tissue. In still another aspect, the methods of the invention include the administration of a relatively low effective dosage of at least one PS agent followed by one or more laser irradiations to completely destroy the hyperproliferative tissue.

In certain additional aspects, the invention encompasses methods that result in the complete eradication of metastasized and undetected hyperproliferative cells.

In an additional aspect, the present invention relates to a system or kit comprising a container which includes instructions for performing the methods of the invention; one or more containers comprising an effective amount of at least one PS agent. In certain additional aspects the systems of the invention optionally include at least one of a device for providing radiation to a tissue, a means for delivering radiation to the tissue, and/or a means for delivering the PS agent.

The above and other aspects, features, and advantages of the present invention will become apparent from the following description read in conjunction with the accompanying drawings.

DETAILED DESCRIPTION

Photodynamic therapy is a treatment based on the differential uptake of photosensitizers (PS) by hyperproliferative tissue. After a specific time interval (drug-light-interval, DLI), hyperproliferative tissue is irradiated resulting in the production of destructive singlet oxygen in the target tissue. This results in destruction of the cellular parts of hyperproliferative tissue. The superficial destructed cells attached to the main tumor mass stimulate the immune system by triggering a localized inflammatory immune response.

Incomplete direct tumor destruction leads to an unexpected eradication of the tumor mass. The theory is that leaving necrotized tumor tissue in-situ allows the tumor to undergo the natural immune system degradation by white blood cells and macrophages. This process exposes fragments of the tumor tissue including but not limited to protein fragments, inter-cellular components, and leukotrienes, to the immune system, which can mediate inflammatory action. This activates an immune response to the residual tumor mass which expedites complete eradication of the tumor.

Thus, the invention is based, at least in part, on the surprising and unexpected discovery that by administering PDT more than once (i.e., Fractionated-PDT), and at different time points and/or at different dose regimens, one can advantageously recruit the patient's innate and adaptive immune systems, resulting in improved clinical outcomes.

In one aspect, the present invention comprises photodynamic therapy (PDT) methods to treat primary sites of hyperproliferative tissue and induce long term, tumor specific immunity for regression and eradication of distant metastases. Leaving necrotized tissue in-situ allows the tumor/tissue to undergo natural immune system degradation by the phagocytotic action of white blood cells (WBC) and macrophages. This process exposes protein fragments, intercellular components, leukotrienes, and other fragments of the tumor tissue to phagocytosis. Phagocytosis augments the immune system response which aids complete eradication of the residual tumor mass.

In certain aspects, the treatment methods or regimen comprises the partial or fractional application of PDT with several applications, spaced in time, to permit a patient's immune system to react to dead tissue generated by each fractional application. If the primary tumor has not been completely destroyed by the previous PDT applications, a final dose of PDT treatment is administered. The dead tumor cells and debris from fractional-PDT stimulates the immune system. This regimen can stimulate the immune response once or several times, depending on the number of fractional-PDT applications employed. Once activated, the immune system can help reduce or eliminate secondary tumors and metastastic tumors. Additional methods and instruments suitable for use in the methods of the invention are disclosed in U.S. Provisional Patent Application Ser. No. 61/074,796, entitled: "Enhanced Photodynamic Therapy Treatment and Instrument; filed Jun. 23, 2008, which is hereby incorporated by reference in its entirety for all purposes.

In an exemplary embodiment, the invention comprises a method for performing a Photodynamic Therapy (PDT) comprising the steps of: A method for performing Photodynamic Therapy (PDT) comprising the steps of: a. administering to a patient an effective amount of at least one photosensitizer; b. allowing a first period of time to elapse (referred to as the "drug-light interval" (DLI)); c. irradiating a tissue site with an effective amount of radiation at an effective wavelength; d. allowing a second period of time to elapse and repeating, one or more times, steps (a)-(c), wherein the second period of time is sufficient to allow stimulation of the patient's immune system.

In certain embodiments, the above steps are repeated multiple times until complete destruction of the diseased tissue (e.g., tumor) is achieved. The number of repetitions can depend on a number of factors, including, the type of hyperproliferative disease or disorder, the hyperproliferative tissue or tumor size, and/or the number of hyperproliferative tissue sites or tumors. Furthermore, the irradiation can be directed to the entire diseased tissue or portion thereof.

In general, in the methods of the invention the interval between the administration of the PS agent and the irradiation is a time sufficient to allow systemic distribution of the PS agent to the target site (i.e., hyperproliferative tissue or cell). This time may vary based upon a number of factors, including the PS agent used and method of administration (e.g., locally versus systemically), but is typically between about 1 and about 110 hours, more likely between about 90 and about 110 hours when systemically administered. Additionally, in the methods of the invention the interval between an irradiation step and a subsequent administration of a PS agent is the amount of time sufficient to allow stimulation of the patient's natural immune system, for example, the adaptive immune system.

Unexpectedly, the inventors have discovered that the time interval between the first and subsequent PDT treatments is important for immune system recruitment. In any of the embodiments described herein the interval between the first and subsequent PDT treatments, which can include a subsequent irradiation step, can range from ten minutes to one month. In certain embodiments the time interval between sequential PDT treatments can be: (in minutes) 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60; (in hours)

1, 2, 3, 4, 5, 6, 7, 8, 9, 10, 11, 12, 13, 14, 15, 16, 17, 18 19, 20, 21, 22, 23, 24; (in days) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31. As those of skill in the art will recognize, the particular time interval will depend on a number of factors, for example, the age, height, and weight of the patient; the disease type and distribution; and the selection of PS agent. The most effective time intervals can be empirically determined easily and without undue experimentation using known methods and/or model systems, for example, animal models, in view of the present teachings.

In certain embodiments, the methods of the invention comprise at least one of the administering an effective amount of at least one PS agent, administering at least one fractional-PDT low dose regimen, administering at least one fractional-PDT high dose regimen or a combination thereof. In any of the embodiments described herein, the PS agent can be administered either systemically or locally; i.e., directly to the tissue site. The method is particularly useful for the treatment of primary tumors, and secondary and metastatic tumors, which conventional or classic PDT cannot fully eradicate.

In another aspect, the methods of the invention include performing a fractional-PDT regimen which stimulates the patient's natural immune system to produce tumor-specific antibodies. Stimulation of a patient's natural immune system can be assessed by monitoring the patient's blood serum for tumor specific antigens. Ex-vivo antigen identification will permit manufacture and subsequent treatment with tumor specific antibodies creating useful therapies to re-treat a relapsed patient or initial treatment of newly diagnosed patients by passive transfer of immunity using antiserum.

The methods of the invention are useful not only for cancer treatments but also for the treatment of any disease associated with the presence of foreign or diseased cells which when damaged can stimulate the normal immune inflammatory process, induce phagocytosis, and lead to the production of disease specific antigens.

Traditionally, PDT techniques are used to locally eradicate the tumor by providing an effective amount of PS, light, and singlet oxygen in the tumor mass. Therefore, they are limited to the tumors or diseases where all three objectives can be achieved. However, an advantage of the fractional-PDT methods of the present invention is that they have no such limitations; as it uses fractional degradation of target diseased tissues to trigger an enhanced immune system response, to eliminate the hyperproliferative tissue and similar foreign cells throughout the body.

The word photosensitizer, as used herein, refers generally to and includes photosensitizing agents, photosensitizing delivery systems, and photosensitizer derivatives from a parent structure or a prodrug generally known to those of skill in the art. A variety of molecules can be used as photosensitizers in the new methods and are described further below. In certain embodiments, a photosensitizer is a molecule capable of the photochemical conversion of an irradiating energy into radical and cytotoxic species (as described above), which in turn mediates the desired biological effect on target cells and/or blood vessels. In certain other embodiments, more than one photosensitizer can be used in the methods of the invention.

By way of example, the photosensitizing agent used in any of the methods of the invention can be, for example, a porphyrin, porphyrinogen, hematoporphyrin, pheophorbide, chlorin, bacteriochlorin, iso-bacteriochlorin and dihydro- and tetrahydro-tetrapyrroles, indium-bound pyropheophorbides, pyrrole-derived macrocyclic compounds, porphyrins, chlorins, phthalocyanines, indium chloride methylpyropheophorbide, naphthalocyanines, porphycenes, porphycyanines, pentaphyrins, sapphyrins, benzochlorins, chlorophylls, azaporphyrins, 5-amino levulinic acid, purpurins, anthracenediones, anthrapyrazoles, aminoanthraquinone, phenoxazine dyes, and derivatives thereof. More specifically, the photosensitizers can be the same or different and can be, independently, haematoporphyrin derivatives, benzoporphyrin derivative-monoacid ring A, meta-tetrahydroxyphenyl-chlorin-, 5-aminolevulinic acid, tin ethyl etiopurpurin, boronated protoporphyrin, lutetium texaphyrin, phthalocyanine-4,2-(1-hexyloxyethyl)-2-devinyl pyropheophorbide-alpha, or taporfin sodium. One specific useful photosensitizer is indium, chloro[methyl 9-ethenyl-14-ethyl-4,8,13,18-tetramethyl-20-oxo-3-phorbinepropanoato (2-)-N23, N24, N25, N26]-, [SP-4-2-(3S-trans)]-(9CI)) (MV6401™).

In still other embodiments, the photosensitizer is capable of absorbing electromagnetic radiation and transferring that energy by a chemical process to desired target molecules, to biological complexes and/or cellular or tissue structures. Such an energy transfer may occur in a photochemical process similar to photosynthesis in plants. In certain embodiments, photosensitizers useful for the described methods include, but are not limited to, the following naturally occurring or synthetic compounds and derivatives thereof: pyrrole derived macrocyclic compounds, porphyrins, chlorins, bacteriochlorins, isobacteriochlorins, phthalocyanines, naphthalocyanines, porphycenes, porphycyanines, pentaphyrins, sapphyrins, benzochlorins, chlorophylls, azaporphyrins, the metabolic porphyrinic precusor 5-amino levulinic acid, PHOTOFRIN®, synthetic diporphyrins and dichlorins, phenyl-substituted tetraphenyl porphyrins (e.g., FOSCAN® picket fence porphyrins), indium chloride methyl pyropheophorbide (MV64013™), 3,1-meso tetrakis (o-propionamido phenyl) porphyrin, verdins, purpurins (e.g., tin and zinc derivatives of octaethylpurpurin (NT2), and etiopurpurin (ET2)), zinc naphthalocyanines, anthracenediones, anthrapyrazoles, aminoanthraquinone, phenoxazine dyes, chlorins (e.g., chlorin e6, and mono-1-aspartyl derivative of chlorin e6), benzoporphyrin derivatives (BPD) (e.g., benzoporphyrin monoacid derivatives, tetracyanoethylene adducts of benzoporphyrin, dimethyl acetylenedicarboxylate adducts of benzoporphyrin, Diels-Adler adducts, and monoacid ring "a" derivative of benzoporphyrin), low density lipoprotein mediated localization parameters similar to those observed with hematoporphyrin derivative (HPD), sulfonated aluminum phthalocyanine (Pc) (sulfonated AlPc, disulfonated ($AlPcS_2$), tetrasulfonated derivative, sulfonated aluminum naphthalocyanines, chloroaluminum sulfonated phthalocyanine (CASP)), phenothiazine derivatives, chalcogenapyrylium dyes cationic selena and tellurapyrylium derivatives, ring-substituted cationic phthalocyanines, pheophorbide alpha, hydroporphyrins (e.g., chlorins and bacteriochlorins of the tetra(hydroxyphenyl) porphyrin series), phthalocyanines, hematoporphyrin (HP), protoporphyrin, uroporphyrin III, coproporphyrin III, protoporphyrin IX, 5-amino levulinic acid, pyrromethane boron difluorides, indocyanine green, zinc phthalocyanine, dihematoporphyrin, benzoporphyrin derivatives, carotenoporphyrins, hematoporphyrin and porphyrin derivatives, rose bengal, bacteriochlorin A, epigallocatechin, epicatechin derivatives, hypocrellin B, urocanic acid, indoleacrylic acid, rhodium complexes, etiobenzochlorins, octaethylbenzochlorins, sulfonated Pc-naphthalocyanine, silicon naphthalocyanines, chloroaluminum sulfonated phthalocyanine, phthalocyanine derivatives, iminium salt benzochlorins, and other iminium salt complexes, Merocyanin 540, Hoechst 33258, and other DNA-binding fluorochromes, psoralens, acridine compounds, suprofen, tiaprofenic acid, non-steroidal anti-inflammatory drugs, methylpheophorbide-a-(hexyl-ether), and other pheophorbides, furocoumarin hydroperoxides, Victoria blue BO, methylene blue, toluidine blue, porphycene compounds described in U.S. Pat. No. 5,179,120, indocyanines, and any other photosensitizers noted herein, and any combination of any or all of the above.

The "derivative" or "derivatives" of the photosensitizers mentioned above are molecules with functional groups that are attached covalently or non-covalently to the molecule. Examples of functional groups include: hydrogen; a halogen, such as fluoro, chloro, iodo, and bromo; lower alkyl, such as methyl, ethyl, n-propyl, isopropyl, t-butyl, n-pentyl, and the like groups; lower alkoxy, such as methoxy, ethoxy, isopropoxy, n-butoxy, tentoxy, and the like; hydroxy; alkylhydroxy, alkylethers; carboxylic acid or acid salts, such as —$CH_2COOH$, —$CH_2COO^-Na^+$, —$CH_2CH_2COOH$, —$CH_2CH_2COONa$, —$CH_2CH_2CH(Br)COOH$, —$CH_2CH_2CH(CH_3)COOH$, —$CH_2CH(Br)COOH$, —$CH_2CH(CH_3)COOH$, —$CH(Cl)$—$CH_2$—$CH(CH_3)$—$COOH$, —$CH_2$—$CH_2$—$C(CH_3)_2$—$COOH$, —$CH_2$—$CH_2$—$C(CH_3)_2$—$COO^-K^+$, —$CH_2$—$CH_2$—$CH_2$—$CH_2$—$COOH$, $C(CH_3)_3$—$COOH$, $CH(Cl)_2$—$COOH$ and the like; carboxylic acid esters, such as —$CH_2CH_2COOCH_3$, —$CH_2CH_2COOCH_2CH_3$, —$CH_2CH(CH_3)COOCH_2CH_3$, —$CH_2CH_2CH_2COOCH_2CH_3$, —$CH_2CH(CH_3)_2 COOCH_2CH_3$, and the like; sulfonic acid or acid salts, for example, group I and group II salts, ammonium salts, and organic cation salts such as alkyl and quaternary ammonium salts; sulfonylamides such as substituted and unsubstituted benzene sulfonamides; sulfonic acid esters, such as methyl sulfonate, ethyl sulfonate, cyclohexyl sulfonate, and the like; amino, such as unsubstituted primary amino, methylamino, ethylamino, n-propylamino, isopropylamino, 5-butylamino, secbutylamino, dimethylamino, trimethylamino, diethylamino, triethylamino, di-n-propylamino, methylethylamino, dimethyl-sec-butylamino, 2-aminoethanoxy, ethylenediamino, 2-(N-methylamino) heptyl, cyclohexylamino, benzylamino, phenylethylamino, anilino, -methylanilino, N,N-dimethylanilino, N-methyl-N ethylanilino, 3,5-d ibromo-4-anilino, p-toluidino, diphenylamino, 4,4'-dinitrodiphenylamino, and the like; cyano; nitro; a biologically active group; any other substituent that increases the amphiphilic nature of the compounds; or doso- or nido-carborane cages.

The "biologically active group" of the derivative of the photosensitizers mentioned above can be any group that selectively promotes the accumulation, elimination, binding rate, or tightness of binding in a particular biological environment. For example, one category of biologically active groups is the substituents derived from sugars, specifically, aldoses such as glyceraldehyde, erythrose, threose, ribose, arabinose, xylose, lyxose, allose, altrose, glucose, mannose, gulose, idose, galactose, and talose; ketoses such as hydroxyacetone, erythrulose, rebulose, xylulose, psicose, fructose, verbose, and tagatose; pyranoses such as glucopyranose; furanoses such as fructo-furanose; O-acyl derivatives such as penta-O-acetyl-a-glucose; O-methyl derivatives such as methyl a-glucoside, methyl p-glucoside, methyl a-glucopyranoside and methyl-2,3,4,6-tetra-O-methyl glucopyranoside; phenylosazones such as glucose phenylosazone; sugar alcohols such as sorbitol, mannitol, glycerol, and myo-inositol; sugar acids such as gluconic acid, glucaric acid and glucuronic acid, o-gluconolactone, 5-glucuronolactone, ascorbic acid, and dehydroascorbic acid; phosphoric acid esters such as a-glucose 1-phosphoric acid, a-glucose 6-phosphoric acid, a-fructose 1,6-diphosphoric acid, and a-fructose 6-phosphoric acid; deoxy sugars such as 2-deoxy-ribose, rhammose (deoxy-mannose), and fructose (6-deoxy-galactose); amino sugars such as glucosamine and galactosamine; muramic acid and neuraminic acid; disaccharides such as maltose, sucrose and trehalose; trisaccharides such as raffinose (fructose, glucose, galactose) and melezitose (glucose, fructose, glucose); polysaccharides (glycans) such as glucans and mannans; and storage polysaccharides such as a-amylose, amylopectin, dextrins, and dextrans.

Amino acid derivatives are also useful biologically active groups, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagines, and glutamine. Also useful are peptides, particularly those known to have affinity for specific receptors, for example, oxytocin, vasopressin, bradykinin, LHRH, thrombin, and the like.

Other useful biologically active groups are those derived from nucleosides, for example, ribonucleosides such as adenosine, guanosine, cytidine, and uridine; and 2'-deoxyribonucleosides, such as 2'-deoxyadenosine, 2'-deoxyguanosine, 2'-deoxycytidine, and 2'-deoxythymidine.

Another category of biologically active groups that is particularly useful is any ligand that is specific for a particular biological receptor. A "ligand specific for a receptor" is a moiety that binds to a biological receptor, e.g., on a cell surface, and, thus, contains contours and charge patterns that are complementary to those of the biological receptor. Examples of such ligands include: the steroid hormones, such as progesterone, estrogens, androgens, and the adrenal cortical hormones; growth factors, such as epidermal growth factor, nerve growth factor, fibroblast growth factor, and the like; other protein hormones, such as human growth hormone, parathyroid hormone, and the like; neurotransmitters, such as acetylcholine, serotonin, dopamine, and the like; and antibodies. Any analog of these substances that also succeeds in binding to a biological receptor is also included. Particularly useful examples of substituents tending to bind to receptors (and to increase the amphiphilic nature of photosensitizers) include: long chain alcohols, for example, —$C_{12}H_{24}$—$OH$ where —$C_{12}H_{24}$ is hydrophobic; fatty acids and their salts, such as the sodium salt of the long-chain fatty acid oleic acid; phosphoglycerides, such as phosphatidic acid, phosphatidyl ethanolamine, phosphatidyl choline, phosphatidyl serine, phosphatidyl inositol, phosphatidyl glycerol, phosphatidyl 3'-O-alanyl glycerol, cardiolipin, or phosphatidal choline; sphingolipids, such as sphingomyelin; and glycolipids, such as glycosyidiacylglycerols, cerebrosides, and sulfate esters of cerebrosides or gangliosides.

In certain embodiments, photosensitizers useful in the new methods include, but are not limited to, members of the following classes of compounds: porphyrins, chlorins, bacteriochlorins, purpurins, phthalocyanines, naphthalocyanines, texaphyrins, and non-tetrapyrrole photosensitizers. For example, the photosensitizer may be, but is not limited to, PHOTOFRIN®, benzoporphyrin derivatives, tin ethyl etiopurpurin (SnET2), sulfonated chloroaluminum phthalocyanines and methylene blue, and any combination of any or all of the above.

Any compound, molecule, ion, or atom can be examined for its usefulness for the described methods, for example, by testing it in an animal model according to the methods described herein. Such animal models are described in, for example, Bellnier et al., 1995, Photochemistry and Photobiology, 62:896-905; Endrich et al., 1980, Res. Exp. Med., 177:126-134; Tije et al, 1999, Photochem. Photobiol., 69:494-499; Abels et al., 1997, J. Photochem. Photobiol., B40:305-312; Fingar et al., 1992, Cancer Res., 52:4914-

4921; Milstone et al., 1998, Microcirculation., 5:153-171; Kuhnle et al., 1998, J. Thorac. Cardiovasc. Surg., 115:937-944; Scalia et al., 1998, Arterioscler. Thromb. Vasc. Biol., 18:1093-1100; Iida et al., 1997, Anesthesiology, 87:75-81; Dalla Via et al., 1999, J. Med. Chem., 42:4405-4413; Baccichetti, et al., 1992, Farmaco., 47:1529-1541; and Roberts et al., 1989, Photochem. Photobiol., 49:431-438. See, also, U.S. Pat. Nos. 5,965,598; 5,952,329; 5,942,534; 5,913,884; 5,866,316; 5,775,339; 5,773,460; 5,637,451; 5,556,992; 5,514,669; 5,506,255; 5,484,778; 5,459,159; 5,446,157; 5,409,900; 5,407,808; 5,389,378; 5,368,841; 5,330,741; 5,314,905; 5,298,502; 5,298,018; 5,286,708; 5,262,401; 5,244,671; 5,238,940; 5,214,036; 5,198,460; 5,190,966; 5,179,120; 5,173,504; 5,171,741; 5,166,197; 5,132,101; 5,064,952; 5,053,423; 5,047,419; and 4,968,715, which describe photosensitizers useful in the new methods, and are incorporated herein by reference.

In certain methods of the invention, the photosensitizing (PS) agent is administered approximately simultaneously or contemporaneously with an effective amount of one or more immunostimulatory agents, which are known or become known. By way of nonlimiting example, immunostimulatory agents include TNF superfamily molecules such as CD40 ligand; agonists for TLRs; agonists for NAIP, CIITA, HET-E, TP-1-leucine-rich repeat pathway receptors, such as nucleotide-binding and oligomerization domain (NOD)1, NOD2, and cryopyrin; chemokines; ILs; CSFs; IFNs; alarmins; and purinergic $P2X_7$ receptor agonists. Especially effective are combinations of agents which can elicit a massive expansion of antigen-specific $CD8^+$ T cells and show unprecedented efficacy in vaccine and tumor models. For a discussion of a wide spectrum of immunostimulatory agents, see Kombluth et al., *J. Leukocyte Biol.*, 80:1084-1102 (2006), which is incorporated herein by reference in its entirety. As one of skill in the art would recognize, the selection of any particular immunostimulatory agent depends on a number of factors such as potential for drug interaction; light sensitivity; patient age, height, and weight; potential side-effects; etc. . . . , which can be readily assessed on a case-by-case basis.

Photosensitizers and/or immunostimulatory agents as described herein are used in the disclosed methods in "effective amounts," i.e., at a dosage that facilitates the desired biological effects, for example blood vessel and/or tissue destruction, or immune system stimulation. An effective amount or dosage of a photosensitizer in the new methods depends, for example, on a variety of properties of the activating light (e.g., wavelength, energy, energy density, intensity), the optical properties of the target tissue, and properties of the photosensitizer. The upper and lower dosage limits depend on the type of photosensitizer used, and these limits are generally known and standardized by the manufacturers for a variety of photosensitizers. In addition, the photosensitizer dosimetry can be determined empirically by those skilled in the art utilizing well known methods, such as standard dose response measurements. Additional factors for consideration in determining the dosage per administration is the number of administrations to be given, and tumor size or mass, and whether the dosage is to be administered locally (i.e., at the diseased tissue site) or systemically. Thus, in fractional-PDT methods of the invention, the dosage can be lower than typically used with a given photosensitizer so that the total of all fractionated doses can be the same, lower, or higher than the standard dose for a given photosensitizer. As such, in certain embodiments, the effective dose utilized in the fractional-PDT methods of the invention range from about 0.1% to about 100% of the standard or manufacturer's recommended dosage.

Theoretically, the highest effective dose of the photosensitizers is limited by their toxicity to the subject, and the lowest effective dose is limited by the effectiveness of the photosensitizer for treating the disease at the low dose. For those skilled in the art, the examples cited herein provide a methodology that will enable the photosensitizer dosimetry to be determined empirically. Exemplary doses contemplated by the present invention range from about 0.01 to about 10.0 mg/kg body weight (BW), and include, for example, 5.0, 2.5, 1.0, 0.5, 0.2, 0.25, 0.1, 0.09, 0.08, 0.07, 0.06, 0.05, 0.04, 0.03, or 0.02 mg/kg of BW. The dose per administration will depend on the total number of administrations for a given total dose.

In certain embodiments, the methods of the present invention utilize a fractional-PDT regimen consisting of a low dose-PDT or a high dose-PDT administration or a combination thereof. As used herein, the term "low dose-PDT" refers to a regimen with either a reduced dosage of PS or a reduced light dose, but not both. The low dose-PDT regime also encompasses a combination of either low dosage PS and standard light dose or standard dosage PS and low light dose. As used herein, "low dose" indicates a level of light dose or PS dosage that is lower than standard or established values in PDT cancer treatment; i.e., relative to the manufacturer's recommended single dosage amount for the particular PS agent.

In one exemplary embodiment, the fractional-PDT method comprises administering a low dose-PDT comprising a temoporfin [chemical name m-tetrahydroxyphenylchlorin (mTHPC)] dosage of about 0.20 mg/kg, and a low light dose of less than or equal to about 40 $J/cm^2$. In another exemplary embodiment, the low dose-PDT comprises a mTHPC dosage of less than or equal to about 0.20 mg/kg and a standard light dose, for example, about 40 $J/cm^2$.

As used herein, the term "high dose-PDT" refers to a regimen of at least standard dosage PS and at least standard light dose. The term "high dose" indicates a level of light dose or PS dosage which is approximately equal to or higher than the established/standard values in PDT cancer treatment; i.e., relative to the manufacturer's recommended single dosage amount for that PS agent. In an exemplary embodiment, the fractional-PDT method comprises administering a high dose-PDT comprising a mTHPC dosage of at least about 0.20 mg/kg, and a light dose of at least about 40 $J/cm^2$.

In any of the embodiments described herein, the "low dose" or "high dose" may comprise one or more PS agents as described herein or known to those of skill in the art or which becomes known to those of skill in the art.

In any embodiment of the methods of the invention, following the administration of the fractional-PDT regimen, dead tumor cells are left in-situ long enough to stimulate an immune system response. The regimen stimulates the immune response at least once. In one exemplary embodiment of the fractional-PDT methods of the invention, a low dose-PDT is followed by a high dose-PDT, for complete destruction of the tumor. But, in many cases the initial low dose-PDT treatments and immune system response may fully eliminate the diseased tissue without the requirement of a final high dose-PDT; a final low dose-PDT may be administered or the final PDT dose may be omitted.

In another exemplary embodiment, the fractional-PDT regimen is administered using at least one low dose-PDT regimen, followed by administration of at least one low or high dose-PDT. In an alternative embodiment the fractional-PDT treatment regimen is administered using a low dose-PDT, followed by multiple low dose-PDT administrations. In yet another exemplary embodiment, the fractional-PDT regimen is administered using a high dose-PDT followed by multiple low dose-PDT administrations. The tumor size, location and patient response to the treatment will dictate the type of fractional-PDT treatment regime.

The means for delivering activating radiation includes a treatment radiation source that includes one or more individual radiation sources that emit radiation substantially at a wavelength sufficient to activate each chosen PS (e.g., about 652 nm for mTHPC). The treatment radiation source is capable of emitting numerous wavelengths, at least to activate each of the two chosen PS, which can be applied separately, preferably in a predetermined sequence. One currently preferred radiation source includes a diode source, such as a diode laser, an LED, a superluminescent diode, or a high power tapered diode, such as a MOPA diode. The diode source may comprise numerous diodes, such as a diode bar or diode array. Other radiation sources, such as solid state lasers or non-coherent lamps also may be used. The capability of emitting numerous individual wavelengths can be accomplished by including two (or more) radiation emitters that emit selected wavelengths, such as numerous diodes or diode bars.

The treatment radiation source is coupled to a radiation delivery device by suitable coupling means such as a lens system. The radiation delivery device preferably comprises an optical fiber or optical fiber bundle. In one embodiment, the treatment radiation source is coupled to a plurality of optical fibers or optical fiber bundles for delivering radiation simultaneously or substantially simultaneously to a number of locations at or near the tumor. In another embodiment, the treatment radiation source may be coupled to a single optical fiber or fiber bundle, or numerous optical fibers or fiber bundles that are individually coupled to different individual radiation sources comprising the treatment radiation source. Other configurations can be selected to allow for sequential irradiation, and irradiation delivered to multiple locations.

Figure 1:
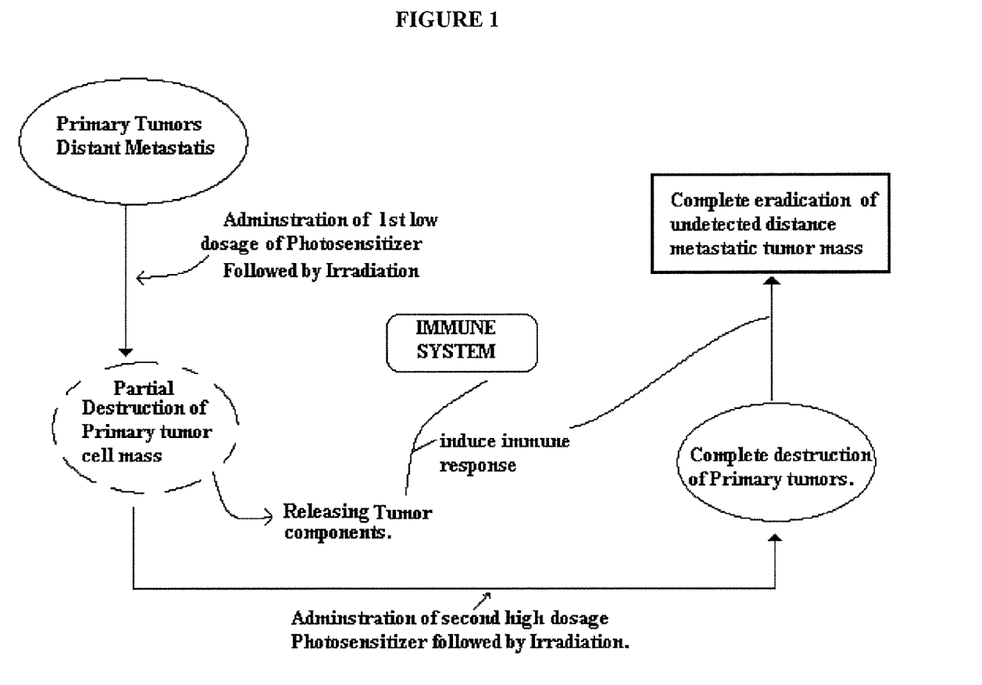
FIG. 1 is a block diagram of the steps involved in administering the PDT for stimulation of the immune system to target primary and metastatic tumors.
Figure 2:
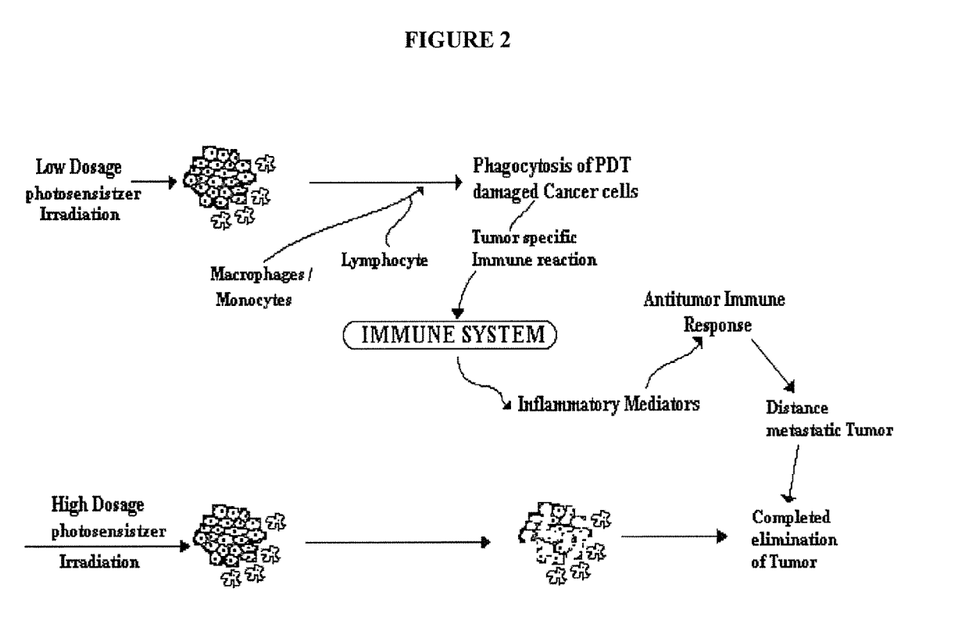
FIG. 2 is a schematic representation of the steps involved in PDT treatment.

As illustrated in FIG. 1 and FIG. 2, after the first fractional-PDT treatment, diseased cells are exposed to the host immune system. The aim of fractional-PDT is the partial destruction of the diseased tissue structure, thus enabling contact between the host diseased cell components and the immune system components. The diseased tissue debris remain in-situ long enough so that the immune system can adequately develop a defense against the antigen. Immune system phagocytes engulf partially destroyed cancer cells, triggering inflammatory mediators and activating T-lymphocyte cells. This can be followed by at least one additional administration of the same or high dose-PDT, which would completely destroy the localized primary diseased tissue mass. Any undetected and distant metastasized diseased tissue mass is eliminated by the PDT stimulated host immunological defense system.

Thus, the fractional-PDT method with immune system activation of the present invention is effective in fighting further cancer cell growth, eliminating and suppressing the body response that permits cancer growth, and preventing cancer metastasis.

In another aspect, the present invention relates to kits and/or systems for performing fractional-PDT treatment, for example, for the treatment of a hyperproliferative disease or disorder which comprises a container including instructions for performing the fractional-PDT methods of the invention; and one or more containers comprising an effective amount of at least one PS agent in a form suitable for systemic or localized administration to a patient. In certain embodiments, the kits or systems of the invention optionally comprise at least one of a device for providing radiation; a means for delivering radiation to the tissue site, for example, a fiber optic line; and/or a means for administering the PS agent to the patient, for example, a syringe having a needle or cannula.

In general, the fractional-PDT methods can be used to treat diseases characterized by the presence of vascular and/or neovascular blood vessels and/or hyperproliferative and/or abnormal cells. Examples of such diseases include cancer, in which case the target tissues include tumor vasculature and cancerous and normal cells. Examples of tumors are gastric cancer, enteric cancer, lung cancer, breast cancer, uterine cancer, esophageal cancer, ovarian cancer, pancreatic cancer, pharyngeal cancer, sarcomas, hepatic cancer, cancer of the urinary bladder, cancer of the upper jaw, cancer of the bile duct, cancer of the tongue, cerebral tumor, skin cancer, malignant goiter, prostatic cancer, cancer of the parotid gland, Hodgkin's disease, multiple myeloma, renal cancer, leukemia, and malignant lymphocytoma. For treatment, the tumor must be penetrable by the activation or activating energy. The described PDT methods can also be used in the treatment of diseased and/or inflamed tissues. For example, the new methods are useful for the treatment of opthalmologic disorders such as age-related macular degeneration, diabetic retinopathy, and choroidal neovascularization; dermatological disorders such as psoriasis and scleroderma; gynecological disorders such as dysfunctional uterine bleeding; urological disorders such as condyloma virus; cardiovascular disorders such as restenosis, intimal hyperplasia, and atherosclerotic plaques; hemangioma; autoimmune diseases such as arthritis; hyperkeratotic diseases; and for hair removal. Normal or diseased tissue on any part of the body can be treated with PDT; thus, normal or abnormal conditions of the hematological system, the lymphatic reticuloendothelial system, the nervous system, the endocrine and exocrine system, the skeletomuscular system including bone, connective tissue, cartilage and skeletal muscle, the pulmonary system, the gastrointestinal system including the liver, the reproductive system, the immune system, the cardiovascular system, the urinary system, the ocular system, and the auditory and olfactory systems can be treated using the new methods.

The fractional-PDT regimen of the invention has additional uses. For example, for additional long-term tumor control, a combined treatment including fractional-PDT in conjunction with the administration of an antineoplastic, anti-angiogenic, and/or cytotoxic therapy may be desirable. Moreover, the therapeutic response of the fractional-PDT methods can be further modified by administering multiple light doses during PDT. The benefit of this new approach is to attack the tumor through different mechanisms of tumor growth, not just stages of cell growth.

In accordance with various embodiments of the present invention, naturally a photosensitizer is used at a dosage less than the dosage that would be so toxic to the subject as to render the described methods unfeasible. Toxicological data for many photosensitizers are known in the art. See, for example, Ouedraogo et al., 1999, Photochem. Photobiol., 70:123-129; Halkiotis et al., 1999, Mutagenesis, 14:193-198; Murrer et al., 1999, Br. J. Cancer, 80:744-755; Mandys et al., 1998, Photochem. Photobiol., 47:197-201; Muller et al., 1998, Toxicol. Lett., 102-103:383-387; Waterfield et al., 1997, Immunopharmacol. Immunotoxicol., 19:89-103; Munday et al, 1996, Biochim. Biophys. Acta, 1311:1-4; Noske et al., 1995, Photochem. Photobiol., 61:494-498; and Lovell et al., 1992, Food Chem. Toxicol., 30:155-160. The toxicity of a photosensitizer at any dosage can be determined using an animal model, for example, a mouse model.

Photosensitizers useful in the described methods can be prepared or formulated for administration in any medium known to the skilled artisan including, but not limited to, tablet, solution, gel, aerosol, dry powder, biomolecular matrix, inhalation.

Photosensitizers useful in the new methods can be administered to a subject by any means known to the skilled artisan including, but not limited to, oral, systemic injection (e.g., venous, arterial, lymphatic), local injection (e.g., slow release formulations), hydrogel polymers, inhalation delivery (e.g., dry powder, particulates), electroporation-mediated, iontophoresis or electrophoresis-mediated, microspheres or nanospheres, liposomes, erythrocyte shells, implantable delivery devices, local drug delivery catheter, perivascular delivery, pericardial delivery, eluting stent delivery.

Photosensitizers can also be conjugated to targeting agents, such as antibodies directed to specific target tissues (e.g., tumor-associated antigens or vascular antigens, such as the ED-B domain). Ligands directed against receptors that are up-regulated in tumor cells can also be conjugated to photosensitizers. For example, low-density lipoprotein (LDL) can be conjugated to photosensitizers to be directed at tumor cells that express the LDL receptor, and estrogen can be used to target photosensitizers to estrogen receptor expressing cells, such as found in hormone-dependent tumors. Liposomes and immunoliposomes can also be used as targeting agents to carry the photosensitizers to specific target tissues.

Once the photosensitizer(s) is administered to the subject, the photosensitizer(s) must be activated by the proper dosage of electromagnetic (EM) radiation, e.g., light. The power, intensity, and duration of the activating radiation used in the new methods, is calibrated so that it facilitates the desired biological effect(s), such as cellular and/or blood vessel destruction at the selected site in the organism of interest when applied to the chosen type and dose of photosensitizer(s). Radiation used in the described methods is preferably calibrated, for example, by choosing the appropriate wavelength, power, power density, energy density, and time of application relative to the times of supply of the photosensitizer(s) to the organism. The wavelength of the radiation can be any wavelength absorbed by the photosensitizer(s), or any other wavelength that mediates the desired biological response in the target tissue. Some examples of type of photosensitizer, dosage, and activating energy are provided above. See, also, U.S. Pat. Nos. 6,013,053; 6,011,563; 5,976,175; 5,971,918; 5,961,543; 5,944,748; 5,910,510; 5,849,027; 5,845,640; 5,835,648; 5,817,048; 5,798,523; 5,797,868; 5,793,781; 5,782,895; 5,707,401; 5,571,152; 5,533,508; 5,489,279; 5,441,531; 5,344,434; 5,219,346; 5,146,917; and 5,054,867, which describe radiation techniques useful in the new PDT methods, and are hereby incorporated herein by reference.

Specific photosensitizers and their activating wavelengths include: MV6401™, 664 nm; PHOTOFRIN™, 630 nm; SnET2, 664 nm; LUTEXT™, 732 nm; benzoporphyrin derivative-monoacid ring A (BPD-MA), 689 nm; mTHPC, 652 nm; 5-aminolevulinic acid (5-ALA, LEVULANT), 635 nm, and boronated protoporphyrin (BOPP), 630 nm. Other useful photosensitizers and their respective activation wavelengths are listed in Dolmans et al., 2003, Nature Reviews, 3:380-387, which is incorporated herein by reference.

In certain embodiments, the wavelength is chosen so that the toxicity to the organism is maintained at a level that does not prohibit the application of the described methods, preferably at a low level, and most preferably at a minimal level. The radiation wavelength used in the new methods is absorbed by the photosensitizer used. In certain embodiments, the radiation wavelength used is such that the absorption coefficient at the chosen wavelength for the photosensitizer used is at least about 5 percent of the highest absorption coefficient for that photosensitizer on the spectrum of electromagnetic radiation of from about 280 nm to about 1700 nm. However, the radiation wavelength may be at least 10, 20, 40, 50, 80, 90, or even 100 percent of the highest absorption coefficient. In other words, the radiation wavelength used in the described methods is such that the absorption coefficient at the chosen wavelength for the photosensitizer used is from about 5 percent to about 100 percent of the highest absorption coefficient for that photosensitizer on the spectrum of electromagnetic radiation of from about 280 nm to about 1700 nm. If more than one photosensitizer is used in the described methods, the above values should apply to at least one of the photosensitizers used, and may apply to all the photosensitizers used.

In certain other embodiments, the wavelength used in the described methods is from about 200 nm to about 2,000 nm, e.g., from about 240 nm to about 1,850 nm, about 280 to about 1,700 nm, about 330 nm to about 1,500 nm, about 380 nm to about 1,250 nm, about 330 nm to about 1,000 nm, about 500 nm to about 800 nm, or about 600 nm to about 700 nm. In certain embodiments, the wavelengths provided above are the wavelengths of the radiation used as it is emitted from the source of radiation used.

Any radiation source producing a wavelength that can activate the photosensitizer used can be employed in the new methods. In certain embodiments, the radiation source used can be a coherent or a non-coherent source including, but not limited to, a laser, a lamp, a light, an optoelectric magnetic device, a diode, or a diode laser. The radiation source must be capable of directing radiation to a site of interest, for example, a laser with optical fiber delivery device, or a fiberoptic insert, or a lens used for interstitial or open field light delivery, or diffusers, including those that may improve penetration of the radiation through the skin or a node of a tumor. Additional methods and instruments suitable for use in the methods of the invention are disclosed in U.S. Provisional Patent Application Ser. No. 61/074,796, entitled: "Enhanced Photodynamic Therapy Treatment and Instrument; filed Jun. 23, 2008, which is hereby incorporated by reference in its entirety for all purposes.

FIG. 1 and FIG. 2 show the steps involved in enhanced PDT with immune system activation and tumor destruction. The invention is further described in the following examples, which do not limit the scope of the invention described in the claims.

EXAMPLE 1

An initial fractional PDT treatment with a low dosage PS of about 0.05 mg/kg of body weight of temoporfin (m-tetrahydroxyphenylchlorin (mTHPC)) or liposome encapsulated mTHPC is administered. After the required drug-light-interval (DLI) an irradiation at 652 nm wavelength with energy of standard light dose of about 40 J/cm$^2$ at about 0.2 W/cm$^2$ is applied. A suitable time interval is allowed for immune system stimulation. Next, a standard dosage PS of about 0.15 mg/kg of body weight is administered followed by irradiation at 652 nm wavelength with energy of low light dose of about 20 J/cm$^2$ at about 0.1 W/cm$^2$.

EXAMPLE 2

An initial fractional-PDT treatment with a low dosage PS of about 0.10 mg/Kg of body weight of mTHPC or liposome encapsulated mTHPC is administered followed by short DLI and irradiation at 652 nm wavelength with energy of standard light dose of about 40 J/cm$^2$ at about 0.2 W/cm$^2$. A suitable time interval is allowed for immune system stimulation before administering a high dosage PS of about 0.20 mg/Kg of body weight followed by short DLI and irradiation at 652 nm wavelength with energy of low light dose of about 15 J/cm$^2$ at about 0.075 w/cm$^2$.

EXAMPLE 3

Fractional-PDT treatment for a larger size tumor comprises administration of low dosage PS of about 0.05 mg/Kg of body weight of mTHPC, followed by short DLI and irradiation at 652 nm wavelength with energy of standard light dose of about 40 J/cm$^2$ at about 0.2 W/cm$^2$. A suitable time interval is allowed for immune system stimulation before administering a high dosage PS of about 0.20 mg/Kg of body weight followed by short DLI and irradiation at 652 nm wavelength with energy of low light dose of about 15 J/cm$^2$ at about 0.075 W/cm$^2$. Next, final administration of a low-dose PDT comprising a low dosage PS of about 0.05 mg/Kg of body weight of mTHPC, followed by short DLI and irradiation at 652 nm wavelength with energy of standard light dose of about 40 J/cm$^2$ at about 0.2 W/cm$^2$.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for performing Photodynamic Therapy (PDT) comprising the steps of:
   a. administering to a patient an effective amount of at least one photosensitizer without an immunopotentiator;
   b. allowing a first period of time to elapse;
   c. irradiating a tissue site with an effective amount of radiation at an effective wavelength;
   d. allowing a second period of time to elapse and repeating, one or more times, steps (a)-(c), wherein the second period of time is sufficient to allow stimulation of the patient's immune system.

2. The method of claim 1, wherein the photosensitizer is administered locally or systemically or both.

3. The method of claim 1, wherein the method further comprises the additional step of
   e. administering an effective amount of at least one photosensitizer,
   f. allowing a third period of time to elapse, and
   g. irradiating with an effective amount of radiation at an effective wavelength, wherein the third period of time is effective in completely eliminating a foreign body or altered cell within the patient.

4. The method of claim 1, wherein the effective amount of at least one photosensitizer administered in step (a) comprises at least one low dose-PDT regimen.

5. The method of claim 4, wherein the low dose-PDT regimen comprises a low dosage of a photosensitizer and a standard light dose.

6. The method of claim 5, wherein photosensitizer is administered at a dosage of at least about 0.05 mg/kg of body weight.

7. The method of claim 5, wherein the standard light dose is approximately 40 J/cm$^2$.

8. The method of claim 2, wherein the low dose-PDT regimen comprises a standard photosensitizer dosage and low light dose.

9. The method of claim 8, wherein the standard photosensitizer dosage is not greater than about 0.20 mg/kg of body weight.

10. The method of claim 8, wherein the low light dose is not greater than about 40 J/cm$^2$.

11. The method of claim 1, wherein the effective amount of at least one photosensitizer administered in step (a) comprises at least one high dose-PDT regimen.

12. The method of claim 11, wherein the high dose-PDT regimen comprises greater than or equal to a standard photosensitizer dosage, and greater than or equal to a standard light dose.

13. The method of claim 12, wherein the standard photosensitizer dosage is about 0.20 mg/kg of body weight.

14. The method of claim 13, wherein the standard light dose is about 40 J/cm$^2$.

15. The method of claim 1, wherein the photosensitizer is at least one member selected from the group consisting of porphyrin, porphyrinogen, hematoporphyrin, pheophorbide, chlorin, bacteriochlorin, iso-bacteriochlorin, and dihydro- and tetrahydro-tetrapyrroles.

16. A system for performing a Photodynamic Therapy (PDT) comprising instructions for performing the method of claim 1: and at least one container comprising an effective amount of at least one photosensitizing agent.

17. The system of claim 16, wherein the system further comprises a means for providing electromagnetic (EM) radiation.

18. The system of claim 17, wherein the system further comprises a means for delivering EM radiation to the tissue site.

19. The system of claim 18, wherein the system further comprises a means for administering the photosensitizing agent to a patient.

20. A method for treating a hyperproliferative disease or disorder comprising the steps of:
   a. administering to a patient a low dose of at least one photosensitizer without an immunopotentiator;
   b. allowing a first period of time to elapse;
   c. irradiating a tissue site with an effective amount of radiation at an effective wavelength;
   d. allowing a second period of time to elapse;
   e. administering to the patient at least one of a standard dose, a low dose, or a high dose of at least one photosensitizer without an immunopotentiator; and
   f. allowing a third period of time to elapse; and
   g. irradiating the tissue site with an effective amount of a radiation at an effective wavelength, wherein the period of time of step (d) or step (f), or both, is sufficient to allow stimulation of the patient's immune system.

21. The method of claim 20, wherein the method comprises the additional step of administering to a patient a low dose of at least one photosensitizer, allowing another period of time to elapse, and irradiating with an effective amount of radiation at an effective wavelength, wherein the final low dose-PDT is sufficient to destroy any remaining hyperproliferative tissue.

22. The method of claim 1, wherein the photosensitizer is further administered in combination with one or more immunostimulatory agents.

23. The method of claim 1, further comprising after step (c) but before step (d), the additional step of allowing another period of time to elapse, and irradiating the tissue site again with an effective amount of radiation at an effective wavelength.

24. The method of claim 20, wherein the photosensitizer is further administered in combination with one or more immunostimulatory agents.

25. The method of claim 20, further comprising after step (c) but before step (d), the additional step of allowing another period of time to elapse, and irradiating the tissue site again with an effective amount of radiation at an effective wavelength.

* * * * *